(12) United States Patent
Domingo (10) Patent No.: US 9,724,088 B2
(45) Date of Patent: Aug. 8, 2017

(54) ARTHROSCOPIC MENISCAL REPAIR SYSTEMS AND METHODS

(71) Applicant: Cayenne Medical, Inc., Scottsdale, AZ (US)

(72) Inventor: Nicanor A. Domingo, Santa Clara, CA (US)

(73) Assignee: Cayenne Medical, Inc., Scottsdale, AZ (US)

( * ) Notice: Subject to any disclaimer, the term of this patent is extended or adjusted under 35 U.S.C. 154(b) by 7 days.

(21) Appl. No.: 14/466,661

(22) Filed: Aug. 22, 2014

(65) Prior Publication Data

US 2015/0051622 A1    Feb. 19, 2015

Related U.S. Application Data

(62) Division of application No. 12/398,100, filed on Mar. 4, 2009, now Pat. No. 8,814,885.

(Continued)

(51) Int. Cl.
*A61B 17/04* (2006.01)
*A61B 17/12* (2006.01)
(Continued)

(52) U.S. Cl.
CPC ...... *A61B 17/0469* (2013.01); *A61B 17/0482* (2013.01); *A61B 17/0625* (2013.01);
(Continued)

(58) Field of Classification Search
CPC . A61B 17/04; A61B 17/0469; A61B 17/0482; A61B 2017/0472;
(Continued)

(56) References Cited

U.S. PATENT DOCUMENTS

| 4,493,323 A | 1/1985 | Albright et al. |
| 5,133,723 A | 7/1992 | Li et al. |

(Continued)

FOREIGN PATENT DOCUMENTS

| EP | 1598017 A1 | 11/2005 |
| EP | 1862125 A2 | 5/2007 |

(Continued)

OTHER PUBLICATIONS

International Search Report and Written Opinion from Application No. PCT/US09/36072, mailed Jan. 14, 2010.

(Continued)

*Primary Examiner* — Melanie Tyson
(74) *Attorney, Agent, or Firm* — Schwegman Lundberg & Woessner, P.A.

(57) ABSTRACT

An arthroscopic meniscal tear repair device includes a catch needle and a transfer needle, which are pierced into a torn meniscus and advanced past the tear. Suture is transferred by a suture needle from the transfer needle through the meniscus and into the catch needle. The catch needle has an internal mechanism that retains the suture. The suture needle is then retracted back to its home position inside the transfer needle, leaving the free end of the suture across the meniscus and in the catch needle. The device is then retracted out of the meniscus, leaving behind a stitch across the meniscal tear inside the meniscus. A pre-tied knot of suture is then slid down the device and cinched up using a knot pusher having a dilation tip, thus completing the repair.

10 Claims, 9 Drawing Sheets

Related U.S. Application Data (60) Provisional application No. 61/033,639, filed on Mar. 4, 2008.

(51) Int. Cl.
*A61B 17/062* (2006.01)
*A61B 17/06* (2006.01)

(52) U.S. Cl.
CPC *A61B 17/06066* (2013.01); *A61B 2017/0472* (2013.01); *A61B 2017/0474* (2013.01); *A61B 2017/0475* (2013.01); *A61B 2017/0477* (2013.01); *A61B 2017/061* (2013.01); *A61B 2017/06042* (2013.01); *A61B 2017/06095* (2013.01)

(58) Field of Classification Search
CPC .... A61B 2017/0474; A61B 2017/0475; A61B 2017/0477
See application file for complete search history.

(56) References Cited

U.S. PATENT DOCUMENTS

| | | | |
|---|---|---|---|
| 5,178,628 A | 1/1993 | Otsuka et al. | |
| 5,234,443 A | 8/1993 | Phan et al. | |
| 5,250,055 A | 10/1993 | Moore et al. | |
| 5,300,078 A | 4/1994 | Buelna | |
| 5,324,298 A | 6/1994 | Phillips et al. | |
| 5,330,488 A | 7/1994 | Goldrath | |
| 5,364,407 A | 11/1994 | Poll | |
| 5,437,680 A | 8/1995 | Yoon | |
| 5,462,560 A | 10/1995 | Stevens | |
| 5,722,981 A | 3/1998 | Stevens | |
| 5,769,862 A | 6/1998 | Kammerer et al. | |
| 5,895,395 A | 4/1999 | Yeung | |
| 5,908,426 A | 6/1999 | Pierce | |
| 6,096,051 A | 8/2000 | Kortenbach et al. | |
| 6,162,209 A | 12/2000 | Gobron et al. | |
| 6,258,106 B1 | 7/2001 | Leonard | |
| 6,635,065 B2 | 10/2003 | Burbank et al. | |
| 6,638,286 B1 | 10/2003 | Burbank et al. | |
| 6,884,249 B2 | 4/2005 | May et al. | |
| 6,997,933 B2 | 2/2006 | Bittar | |
| 7,048,749 B2 | 5/2006 | Kortenbach et al. | |
| 7,094,246 B2* | 8/2006 | Anderson | A61B 17/0467 606/139 |
| 7,118,583 B2 | 10/2006 | O'Quinn et al. | |
| 7,232,448 B2 | 6/2007 | Battles et al. | |
| 7,306,613 B2 | 12/2007 | Kawashima et al. | |
| 7,326,222 B2 | 2/2008 | Dreyfuss et al. | |
| 7,381,210 B2 | 6/2008 | Zarbatany et al. | |
| 7,918,868 B2* | 4/2011 | Marshall | A61B 17/0469 606/139 |
| 8,177,795 B2 | 5/2012 | Niese et al. | |
| 8,814,885 B2 | 8/2014 | Domingo | |
| 2002/0068951 A1 | 6/2002 | Burbank et al. | |
| 2003/0181926 A1 | 9/2003 | Dana et al. | |
| 2004/0249393 A1 | 12/2004 | Weisel et al. | |
| 2005/0033325 A1 | 2/2005 | May et al. | |
| 2005/0187519 A1 | 8/2005 | Harris et al. | |
| 2005/0288690 A1 | 12/2005 | Bourque et al. | |
| 2006/0069399 A1* | 3/2006 | Weisel | A61B 17/0483 606/148 |
| 2006/0178680 A1 | 8/2006 | Nelson et al. | |
| 2006/0282088 A1 | 12/2006 | Ryan | |
| 2007/0149986 A1 | 6/2007 | Morris et al. | |
| 2007/0255306 A1 | 11/2007 | Conlon et al. | |
| 2008/0091219 A1 | 4/2008 | Marshall et al. | |
| 2008/0140091 A1 | 6/2008 | DeDeyne et al. | |
| 2008/0154286 A1 | 6/2008 | Abbott et al. | |
| 2009/0143806 A1 | 6/2009 | Witt et al. | |

FOREIGN PATENT DOCUMENTS

| | | |
|---|---|---|
| GB | 2325165 A | 11/1998 |
| WO | WO-9302625 A1 | 2/1993 |
| WO | 9508950 A1 | 4/1995 |
| WO | 9747246 A1 | 12/1997 |
| WO | 9903402 A1 | 1/1999 |
| WO | 0126588 A1 | 4/2001 |
| WO | 03077771 A1 | 9/2003 |
| WO | WO-2007139785 A2 | 12/2007 |

OTHER PUBLICATIONS

Sgaglione, Meniscus Reapir: Update on New Techniques, Techniques in Knee Surgery, Dec. 2002, 113-127, 1-2.

Carter, Meniscus Repair 2007, Techniques in Knee Surgery, Dec. 2007, 233-241,6-4.

Fukushima, et al., New Meniscus Repair by an All-Inside Knot Suture Technique, Arthroscopy: The Journal of Arthroscopic & Related Surgery, Jun. 2005, 768.e1-768.e10, 21-6.

Lambert et al., Arthroscopic Meniscus Repair with Sutures: Outside-In, Sports Medicine & Arthroscopy Review, Mar. 2004, 25-36, 12-1.

In-Seop Park, New Meniscus Repair Technique for Peripheral Tears near the Posterior Tibial Attachment of the Posterior Horn of the Medial Meniscus, Arthroscopy: The Journal of Arthroscopic & Related Surgery, Aug. 2006, 908.e1-908.e4, 22-8.

Morgan, "All-Inside" Arthroscopic Meniscus Repair, Sports Medicine and Arthroscopy Review, Summer 1993, 1-3.

Reish et al., FasT-Fix Meniscus Repair, Techniques in Knee Surgery, Sep. 2007, 161-167, 6-3.

Prasad et al.; Tribiology of tungsten disulfide-nanocrystalline zinc oxide adaptive lubricant films from ambient to 500 degrees C; Wear, vol. 237, issue 2, Feb. 2000, pp. 186-196.

Supplementary European Search Report issued in connection with corresponding EP App. No. 09718279A, dated eb. 24, 2014.

"U.S. Appl. No. 12/398,100, Final Office Action mailed Dec. 12, 2011", 9 pgs.

"U.S. Appl. No. 12/398,100, Non Final Office Action mailed May 12, 2011", 11 pgs.

"U.S. Appl. No. 12/398,100, Notice of Allowance mailed Apr. 17, 2014", 10 pgs.

"U.S. Appl. No. 12/398,100, Preliminary Amendment filed Sep. 15, 2010", 7 pgs.

"U.S. Appl. No. 12/398,100, Response filed Apr. 20, 2012 to Final Office Action mailed Dec. 12, 2011", 11 pgs.

"U.S. Appl. No. 12/398,100, Response filed Nov. 14, 2011 to Non Final Office Action mailed May 12, 2011", 10 pgs.

"European Application Serial No. 09718279.4, Decision to grant mailed Dec. 10, 2015", 2 pgs.

"European Application Serial No. 09718279.4, Intention to grant mailed Jun. 12, 2015", 6 pgs.

"European Application Serial No. 09718279.4, Intention to grant mailed Oct. 23, 2015", 6 pgs.

"European Application Serial No. 09718279.4, Response filed Sep. 15, 2014 to Extended European Search Report mailed Feb. 24, 2014", 9 pgs.

"International Application Serial No. PCT/US2009/036072, international Preliminary Report on Patentability mailed Sep. 16, 2010", 7 pgs.

* cited by examiner

ARTHROSCOPIC MENISCAL REPAIR SYSTEMS AND METHODS

This application is a divisional application under 35 U.S.C. 120 of commonly assigned U.S. patent application Ser. No. 12/398,100, entitled Arthroscopic Meniscal Repair Systems and Methods, filed Mar. 4, 2009, now issued as U.S. Pat. No. 8,814,885, which in turn claims the benefit under 35 U.S.C. 119(e) of the filing date of Provisional U.S. Application Ser. No. 61/033,639, entitled Arthroscopic Meniscal Repair System, filed on Mar. 4, 2008. Each of the above referenced applications are expressly incorporated herein by reference, in their entirety.

BACKGROUND OF THE INVENTION

The present invention relates to surgical repair of meniscal tears, and more particularly to a unique arthroscopic handheld device and methods for repairing meniscal tears by passing suture within the meniscus through the tear.

There are two meniscuses in each knee, the medial meniscus, and the lateral meniscus, each of which comprises fibrocartilage. The meniscuses protect the articular cartilage on the surfaces of the femur and the tibia. Historically, torn portions of a meniscus were simply surgically removed. However, over time, it has become known in the field that removing substantial portions of the meniscus often accelerates the onset of osteoarthritis and other complications which develop when the shock absorbing meniscuses in the knee are absent. Most tears of the meniscus do not heal on their own, because of a very limited blood supply, but, using modern techniques, many tears can be surgically repaired, thus avoiding the need to remove meniscal portions.

Current meniscal repair methods and devices include both open surgical and arthroscopic techniques. Some repair approaches utilize suture only, others utilize anchors only, while still others are hybrid techniques which employ both suture and anchor devices.

Traditional early prior art arthroscopic meniscal repair methods began with a complicated suture only, "inside outside" technique. These techniques involved several access ports into the surgical site, and several instrument exchanges during the procedure, increasing surgical time and complexity. Because of this, the required surgical skill to effectively execute these arthroscopic procedures was quite high. A benefit to the early conventional methods were that only suture was left behind, thus eliminating the risk of loose bodies in the knee space as well as abrasion to the articular cartilage from hard plastic or metal implants.

A later surgical technique that was developed involved a plastic implant with no suture. The implant had a dart shape to it with barbs that, when inserted into the meniscus, would resist backing out. A benefit to this type of technology was that it didn't require numerous ports or instrument exchanges. This was a much easier method than the suture-only method discussed above. The downside was that it left a plastic head in the articular space which caused abrasion to the femoral condyle articular cartilage.

A still later conventional meniscal repair technique that has been developed is a hybrid involving both an implant and suture. The benefit to this hybrid approach is that the practitioner gained the ease of the implant technique, as discussed above, but there was no exposed plastic implant in the articular space. The downside risk that still exists with this approach is that of a hard plastic loose body remaining at the procedural site. Should some sort of failure occur, the hard plastic implant may come loose and cause damage in the articular space.

What is needed, therefore, is an arthroscopic meniscal repair system and technique which combines the ease of the prior art implant procedures, while eliminating the risk that comes with a hard plastic implant.

SUMMARY OF THE INVENTION

The invention described here are novel methods and devices for arthroscopic meniscal repair that will improve the clinical outcome of meniscal repair procedures and are suitable for general adoption by practitioners. The invention described herein is an all suture approach with the ease of a single working portal, pre-tied knot, single handed device that includes a pre-tied knot.

More particularly, there is provided a device for repairing a tear in a portion of tissue, which comprises a proximal actuator portion, a transfer needle extending distally from the proximal actuator portion and having a distal tip for piercing tissue, and a catch needle extending distally from the proximal actuator portion and having a distal tip for piercing tissue. A suture needle is disposed in the transfer needle, and is extendable from the transfer needle toward the catch needle and retractable from the catch needle toward the transfer needle, upon actuation by the proximal actuator portion. A hook is provided on the suture needle for retaining a length of suture. Advantageously, a retainer in the catch needle is provided for retaining suture in the catch needle when the suture needle is withdrawn from the catch needle back toward the transfer needle.

Preferably, the proximal actuator portion comprises a handle having a suture needle advancement lever disposed thereon, wherein the suture needle is advanced or retracted upon actuation or release of the lever. The transfer needle comprises a window disposed laterally thereon, through which the suture needle is extended or retracted. The catch needle also comprises a window disposed laterally thereon, through which the suture needle is extended or retracted. to enter or leave the catch needle. A second window is disposed on the catch needle on a side opposed to the side on which the first window is disposed, through which a distal end of the suture needle extends when the suture needle is fully extended into the catch needle.

Preferably, the hook on the suture needle is configured so that when the suture needle is retracted in a direction from the catch needle back into the transfer needle, the suture retained thereon is released. This configuration, in the illustrated embodiment, is that of an open slot.

The suture retainer in the catch needle more particularly comprises a plunger, disposed in the catch needle, wherein the plunger is extendable in a distal direction to retain the suture when the suture needle is retracted from the catch needle by clamping the suture within the catch needle.

The suture needle is designed to be sufficiently flexible that it attains a straightened configuration when housed within the transfer needle, and acquires a bend which assists in directing it toward the catch needle when the distal end of the suture needle extends out of the transfer needle. The transfer needle preferably comprises a redirecting curve therein for assisting in redirecting the suture needle toward the catch needle as it is extended from the transfer needle toward the catch needle. A suture relief slot is disposed in the transfer needle.

A pre-tied knot is provided on the device, and movable distally along the device for cinching suture passed through the tissue tear by the device. A knot pusher is also provided, for cinching down the pre-tied knot onto the tissue being repaired. The knot pusher comprises a dilation tip on a distal end thereof for dilating a suture hole and expediting passage of the pre-tied knot distally into the hole.

In another aspect of the invention, there is provided a device for repairing a tear in a portion of tissue. The inventive device comprises a proximal actuator portion, a first needle extending distally from the proximal actuator portion and having a distal tip for piercing tissue, and a second needle extending distally from the proximal actuator portion and having a distal tip for piercing tissue. Further provided is a suture dispenser for attaching a length of suture between the two needles, and extending the length of suture through the tear to approximate and repair the tear. A pre-tied knot is provided, and movable distally along the device for cinching suture passed through the tissue tear by the device. A knot pusher is provided for cinching down the pre-tied knot onto the tissue being repaired. The knot pusher comprises a dilation tip on a distal end thereof for dilating a suture hole and expediting passage of the pre-tied knot distally into the hole.

In still another aspect of the invention, there is disclosed a method for repairing a tear in a portion of tissue, which comprises a step of advancing first and second needles into the tissue, so that distal ends of each needle are disposed beyond the tear. A suture needle is extended, on which is retained a length of suture from the first needle to the second needle, through the tear. A further step comprises retaining the suture in the second needle. The suture needle is then retracted back into the first needle, following which the first and second needles are retracted from the tissue. Suture is dispensed as the needles are retracted.

The above described retaining step more particularly comprises moving a plunger within the second needle to clamp the suture in place within a lumen of the second needle. This ensures that the suture will be retained within the second needle as the suture needle is retracted therefrom.

The inventive method further comprises a step of sliding a pre-tied knot distally along the suture length toward the location of the tear. The pre-tied knot is then cinched. Following the cinching step, the excess suture extending proximally from the pre-tied knot is cut off. The cinching step more particularly comprises a step of advancing a knot pusher distally to push the knot into a hole from which the suture extends. The knot pusher dilates the suture hole as it is advanced thereinto.

The invention, together with additional features and advantages thereof, may best be understood by reference to the following description taken in conjunction with the accompanying illustrative drawing.

DESCRIPTION OF THE PREFERRED EMBODIMENT

Figure 1:
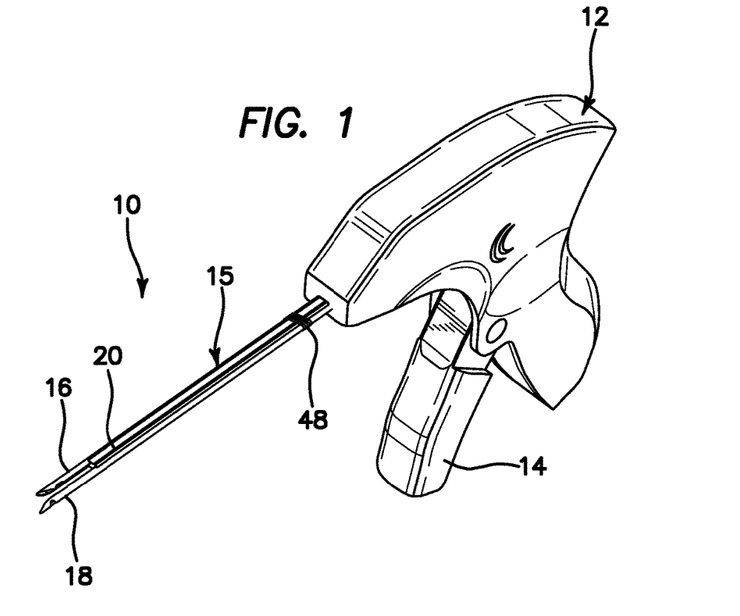
FIG. 1 is an isometric view showing one embodiment of a meniscal repair device constructed in accordance with the principles of the present invention.

Referring now more particularly to the drawings, there is shown in FIG. 1 an embodiment of a meniscal repair device 10 constructed in accordance with the principles of the present invention. The device 10 comprises a handle 12 which has a suture needle advancement lever 14. Distally of the handle 12 are provided an instrument shaft 15, packaging a transfer needle 16, a catch needle 18, and a suture housing 20.

Figure 2:
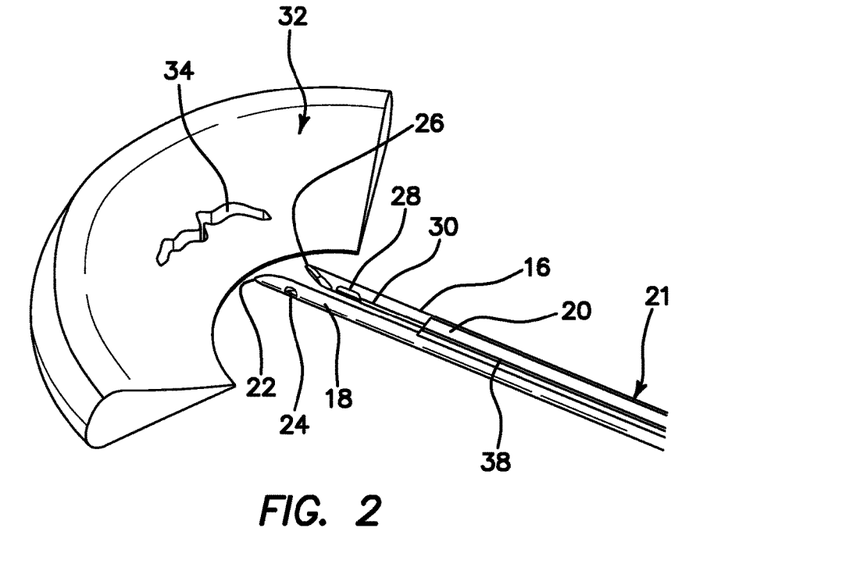
FIG. 2 is an isometric view of the distal end of the meniscal repair device of FIG. 1, inside a patient's knee, as it approaches the meniscus.
Figure 3:
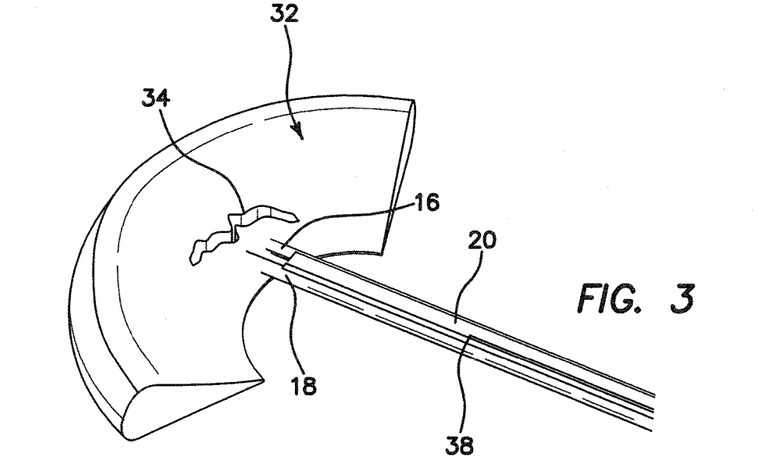
FIG. 3 is an isometric view similar to FIG. 2, illustrating the meniscal repair device after it has advanced into the meniscus.

Now with reference to FIGS. 2 and 3, in addition to FIG. 1, it can be seen that the catch needle 18 has a piercing tip 22. Proximal to the piercing tip 22 on the catch needle 18 is a second suture catch window 24. The transfer needle 16 comprises a piercing tip 26, and a transfer needle window 28 proximal thereto. A suture relief slot 30 is disposed along a length of the transfer needle 16. FIG. 2 illustrates the distal end of the inventive device 10 as it is disposed at a procedural site within the knee joint of a patient, in proximity to a meniscus 32 thereof, having a tear 34 to be repaired.

Figure 4:
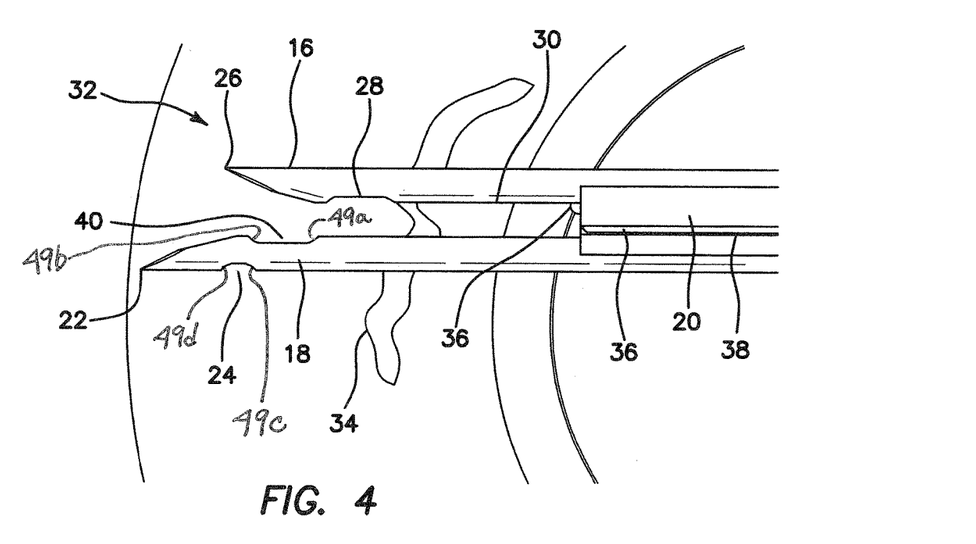
FIG. 4 is a top view, with the meniscus sectioned, and the meniscal repair device in the same position as shown in FIG. 3.
Figure 5:
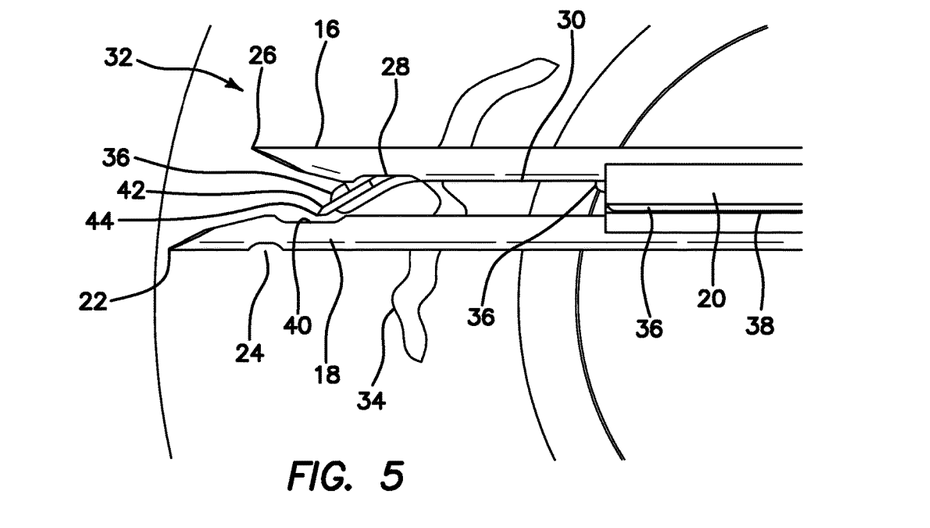
FIG. 5 is a top view similar to FIG. 4, wherein the suture-loaded suture needle is being advanced from the transfer needle through the meniscus toward the capture needle.
Figure 12:
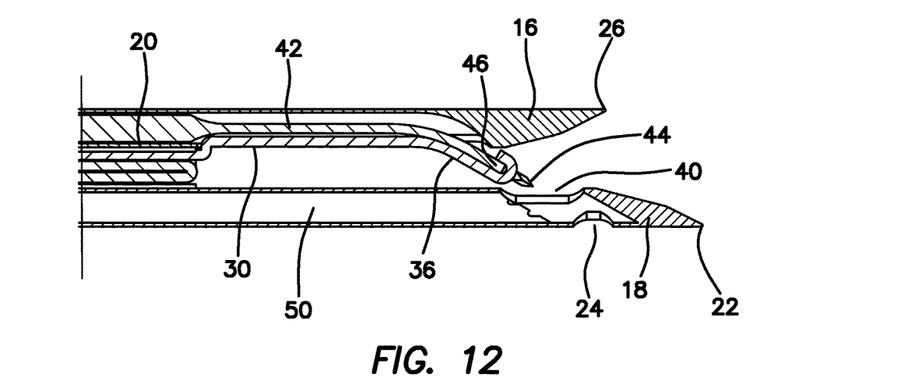
FIG. 12 is a cross-sectional view of the distal end of the inventive meniscal repair device, wherein the suture-loaded suture needle is partially deployed and on its way to the catch needle.

In FIG. 4, additional elements of the inventive device 10 are illustrated. Suture 36 extends along a suture escape slot 38 of the suture housing 20, as shown. A first suture catch window 40 is disposed on the catch needle 18, in generally opposed relation to the second suture catch window 24. In FIG. 5, a suture needle 42 is illustrated, which comprises a suture needle piercing tip 44 and a suture needle hook 46 (FIG. 12).

In operation, in one method of the present invention, with reference initially to all of FIGS. 1-17, the catch needle 18 and the transfer needle 16 are pierced into a meniscus 32 of a patient's knee, having a tear 34 to be repaired, and advanced past the tear 34. The handle 12 is actuated in order to transfer suture 36 (FIG. 4) from the transfer needle 16 through the meniscus 32 and into the catch needle 18. The catch needle 18 has an internal mechanism that retains the suture 36. Upon releasing the suture needle advancement lever 14, which is connected to the suture needle 42 by mechanisms that are well known in the art for this type of advancement and retraction system, the handle 12 automatically returns the suture needle 42 (FIG. 5) back to its home position inside the transfer needle 16, leaving the free end of the suture 36 across the meniscus 32 and in the catch needle 18. It is within the scope of the invention that other configurations of the proximal handle 12 can be used that allow for a single action automatic return system. The device 10 is then retracted out of the meniscus 32, and the suture 36 is dispensed out of the suture housing 20, leaving behind a stitch across the meniscal tear 34 inside the meniscus 32. A pre-tied knot 48 of suture is then slid down the device, cinching up the stitch and thus closing the meniscal tear 34, thus approximating the normal anatomy.

Now, reviewing the inventive method in a sequential fashion, FIG. 2 is an isometric view of the distal end of the meniscal repair device 10 inside a human knee, approaching the meniscus 32. The transfer needle 16 and the catch needle 18 are positioned to pierce the meniscus 32 and cross the meniscal tear 34. The transfer needle 16 and the catch needle 18 are of a relatively small diameter, allowing them to maneuver arthroscopically inside the tight space of the knee. The transfer needle piercing tip 26 and the catch needle piercing tip 22 are preferably sharpened with a triple bevel geometry commonly used in hypodermic needles. It is conceivable that other standard needle points could be used in the inventive device 10 as well.

The suture-loaded suture needle 42 is housed inside the transfer needle 16 and is not visible in FIG. 2. Once the device 10 is pierced into the meniscus 32, and advanced past the tear 34, the suture needle 42 projects out of the transfer needle 16, through the meniscus 32, and into the catch needle 18.

FIG. 3 is an isometric view of the distal end of the meniscal repair device 10, after it has pierced and advanced into the meniscus 32. The catch needle 18 and the transfer needle 16 have been advanced well past the meniscal tear 34. This is essentially the first step of the inventive meniscal repair procedure, which includes locating the meniscal tear 34, piercing the meniscus 32, and advancing the device 10 past the tear 34.

FIG. 4 is a top view of the inventive device 10 in the procedural site, with the meniscus 32 sectioned, and the meniscal repair device 10 in the same position as shown in FIG. 3. Thus, as discussed above, the distal end of the device 10 has entered the meniscus 32 and advanced past the meniscal tear 34. The meniscal repair device 10 may, if desired, be advanced even further to a point beyond the meniscus 32 altogether, and into the knee capsule itself. Also shown in FIG. 4 are the transfer needle window 28, the first suture catch window 40, and the second suture catch window 24. These windows 24, 28, and 40 enable the suture-loaded suture needle 42 to travel from the transfer needle 16 through the meniscus 32 and into the catch needle 18, as will be described below. The suture-loaded suture needle 42 is not visible in FIG. 4, because it is housed inside the transfer needle 16 and has not yet been advanced. The first suture catch window 40 has a leading edge 49a and a trailing edge 49b, while the second suture catch window 24 has a leading edge 49c and a trailing edge 49d, as shown in FIG. 4. As is seen clearly from the figure, the leading edge 49c of the second suture catch window 24 is disposed substantially distal to the leading edge 49a of the first suture catch window 40. Similarly, the trailing edge 49d of the second suture catch window 24 is disposed substantially distal to the trailing edge 49b of the first suture catch window 40. In fact, the trailing edge 49b of the first suture catch window 40 is approximately axially even with the leading edge 49c of the second suture catch window 24, so that substantially all of the second suture catch window is distal to substantially all of the first suture catch window. This arrangement is advantageous because of an improved siting of the suture needle as a result, with substantially less strain on the suture needle and substantially improved retention of the suture in the catch needle by the plunger.

Figure 14:
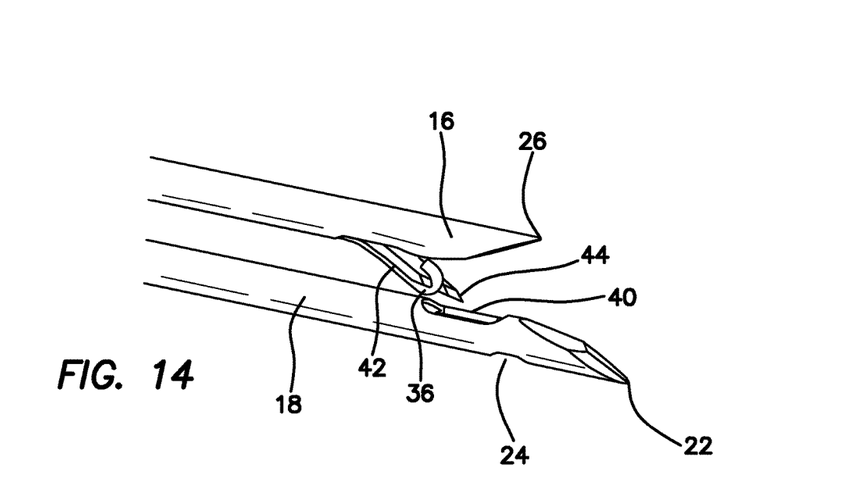
FIG. 14 is a close-up isometric view of the distal end of the inventive meniscal repair device.

FIG. 5 is a top view, similar to FIG. 4, with the meniscus sectioned, which illustrates a method step sequential to that shown in FIG. 4. In FIG. 5, in accordance with the next sequential step in the inventive method, the suture-loaded suture needle 42 is being advanced from the transfer needle 16 through the meniscus 32 and toward the catch needle 18. FIG. 12 is a cross-sectional view of the distal end of the device 10, illustrating the same method step as FIG. 5. As shown in FIG. 12, the suture 36 is hooked onto the suture needle 42, so that the suture needle 42 is "suture-loaded", and is feeding out of the suture housing 20. A catch plunger 50 is in an undeployed state, at this juncture, housed within the catch needle 18. When the suture-loaded suture needle 42 is fully advanced through the second suture catch window 24, then the spring loaded catch plunger 50 is deployed and collides with the suture-loaded suture needle 42. The hook 46 is configured into the suture needle 42 at its distal end so that it can maintain a purchase of the suture 36 during the transferring process. The suture needle 42 also has a needle point or piercing tip 44 configured to give it the ability to pierce through the meniscus 32. The suture needle 42 is sufficiently flexible so that it can be housed in a straightened configuration inside the transfer needle 16 prior to actuation and then take the necessary bend during deployment. The suture-loaded suture needle 42 is shown in transition as it is actuated toward the catch needle 18. The hard stop for this mechanism, or final destination for the suture-loaded suture needle 42, is inside the catch needle 18 and through the second suture catch window 24. FIG. 14 is a close-up isometric view of the distal end of the device 10, also illustrating the step wherein the suture-loaded suture needle 42 is partially deployed and on its way to the catch needle 18. It is important to note that the suture needle hook 46 is configured in a way to retain the suture 36 during advancement of the suture needle 42 and to allow for easy suture release during retraction of the suture needle 42.

Figure 6:
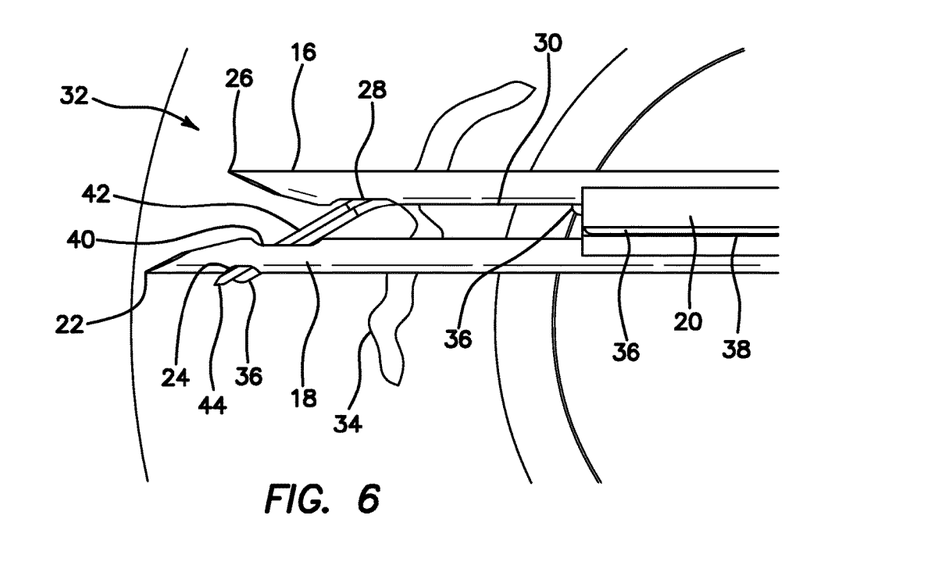
FIG. 6 is a top view similar to FIGS. 4 and 5, wherein the suture-loaded suture needle is fully advanced into the catch needle.
Figure 13:
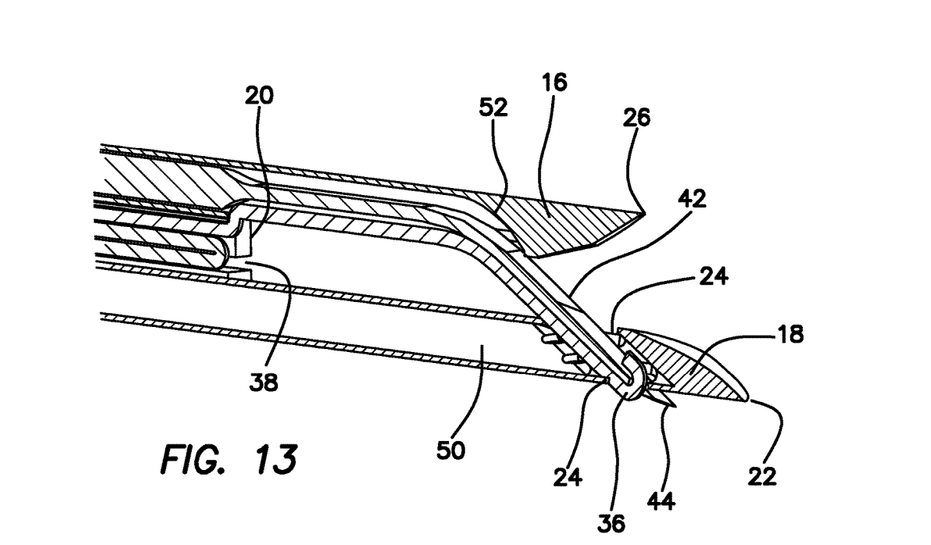
FIG. 13 is an isometric view of the distal end of the meniscal repair device, illustrating the suture-loaded suture needle fully advanced through the second suture catch window.

FIG. 6 is a top view similar to FIG. 5, with the meniscus sectioned, and showing the suture-loaded suture needle 42 after it has fully advanced into the catch needle 18. This maneuver transfers the suture 36 from the transfer needle 16 to the catch needle 18 through the meniscus 32 past the meniscal tear 34. During this maneuver, the suture 36 dispenses freely from the suture housing 20. At this point, the catch plunger 50 (FIG. 12) is advanced, under a spring load, so that it impacts the suture 36 and the suture needle 42. The catch plunger 50 is not visible in FIG. 5 because it is housed inside the catch needle 18. This is important to note because it is the engagement of these components that allows the catch needle 18 to capture the suture 36. FIG. 13 is an isometric view of the distal end of the device, illustrating the same step as that shown in FIG. 6. As illustrated, the transfer needle 16 includes a redirecting curve 52, which is a feature that contributes to the flexing of the suture needle 42 into the catch needle 18. The suture needle 42 can be made of a spring tempered stainless steel or a shape memory type of alloy such as nitinol. It can be manufactured with processes that pre-shape it, thereby allowing it to be advanced out of the transfer needle 16 and into the catch needle 18.

Figure 7:
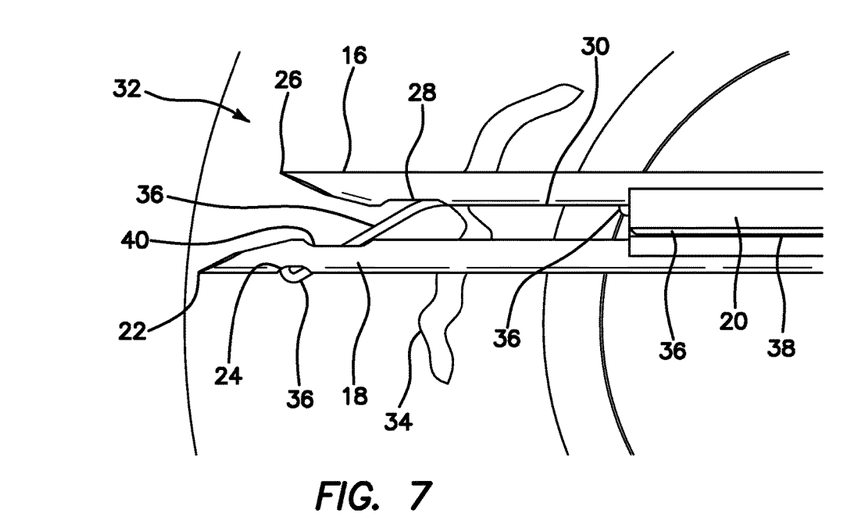
FIG. 7 is a top view similar to FIGS. 4-6, wherein the suture has passed from the transfer needle to the catch needle.

Following the capture step, illustrated in FIGS. 6 and 13, the next step of the inventive process is to retract the suture needle 42 from the catch needle 18 and back into the transfer needle 16, leaving behind the suture 36 in the catch needle 18. FIG. 7 is a top view similar to FIG. 6, with the meniscus sectioned, showing this next step, the suture 36 having already been passed from the transfer needle 16 to the catch needle 18. The suture needle 42 has already been retracted back into the transfer needle 16, leaving behind the suture 36. Two things prevent the suture 36 from retracting back with the suture needle 42. These two things are the spring loaded catch plunger 50 and the design of the suture needle hook 46. The spring loaded catch plunger 50 acts to wedge the suture 36 between it and an inner lumen of the catch needle 18. A tight fit between the tip of the catch plunger 50 and the inner lumen of the catch needle 18, along with the proximal spring force, cause the suture 36 to be retained while the suture needle 42 is retracted. Along with that catch mechanism, the suture needle hook 46 is configured in a way to release the suture 36 during retraction. The hook 46 is essentially an open slot that has no feature to drag or retain the suture 36 during retraction of the suture needle 42.

Figure 8:
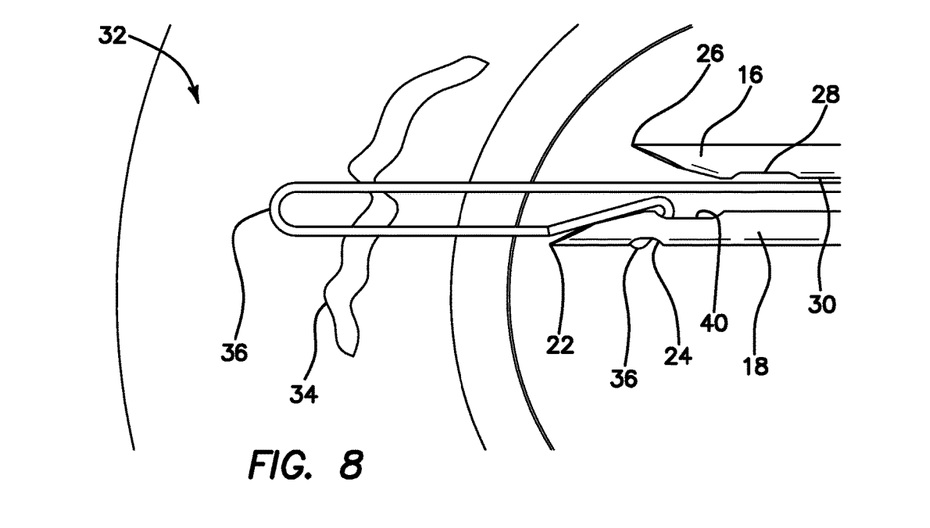
FIG. 8 is a top view similar to FIGS. 4-7, showing the device being retracted out of the meniscus.

The next step in the inventive procedure is to retract the device 10 out of the meniscus 32, thereby dispensing out suture 36. FIG. 8 is a top view, similar to FIG. 7, with the meniscus 32 sectioned, showing the device being retracted proximally from the meniscus 32. The suture 36 is fixed to the catch needle 18, and during device retraction, it pulls the suture 36 through the newly created path past the meniscal tear 34. The suture housing 20 dispenses the suture out, allowing it to pass through the meniscal tear 34. The suture relief slot 30, configured into the transfer needle 16, allows the suture 36 to fully release from the transfer needle 16 and to properly dispense out of the suture housing 20.

Figure 9:
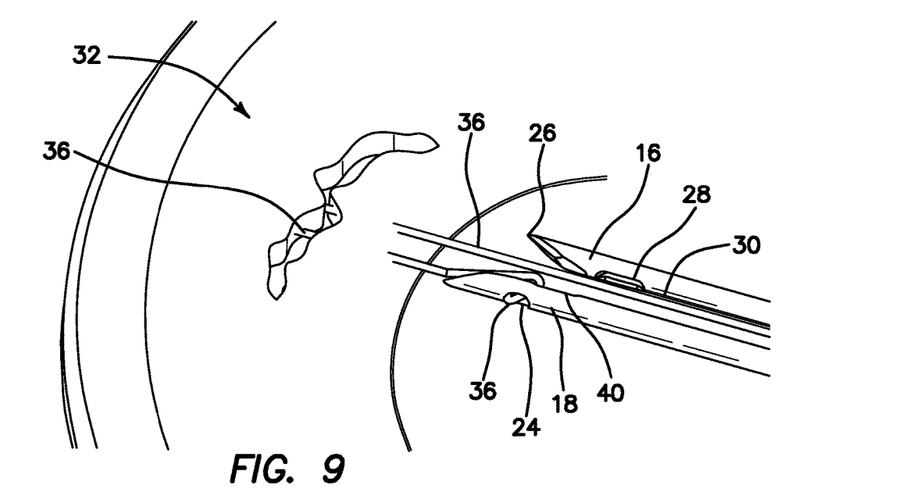
FIG. 9 is an isometric view showing the same step as that shown in FIG. 8.

FIG. 9 is an isometric view illustrating the same step as is shown in FIG. 8. As shown, the device 10 is being retracted proximally from the meniscus 32, leaving behind suture 36 past the meniscal tear 34. At this juncture, the suture 36 has completely released from the transfer needle 16 via the suture relief slot 30, and is dispensing out of the suture housing 20. Not visible is the catch plunger 50 inside the catch needle 18, which is retaining the suture 36. Once the suture housing 20 dispenses out the majority of the suture 36, the pre-tied knot 48 begins to slide down the device 10 toward the meniscus 32.

Figure 10:
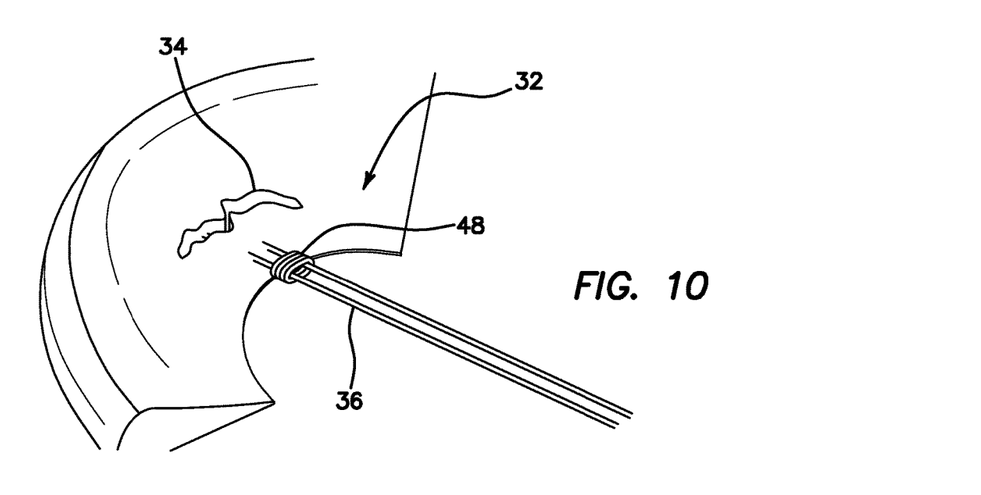
FIG. 10 is an isometric view illustrating the device retracted and a pre-tied knot sliding down toward the meniscus.

FIG. 10 shows an isometric view of the device 10, retracted from the meniscus 32, and with the pre-tied knot 48 sliding down the suture legs 36 toward the meniscus 32. As the device is retracted and the suture 36 dispenses out of the suture housing 20, the pre-tied knot 48 simultaneously begins sliding down the instrument shaft 15 (FIG. 1), then onto the suture legs 36 toward the meniscus 32. This is a standard sliding knot commonly used in arthroscopic surgery.

Figure 11:
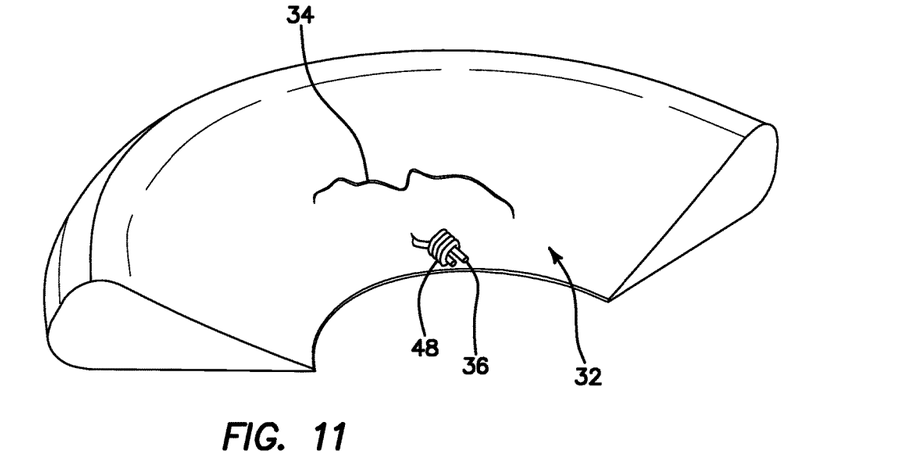
FIG. 11 is an isometric view showing the pre-tied knot cinching up the suture, which closes up the meniscal tear.

FIG. 11 is an isometric view, illustrating the pre-tied knot 48 cinching up the suture 36, and thus closing up the meniscal tear 34. The device 10 has been retracted out of the knee at this point, the pre-tied knot 48 has been slid down into place cinching up the suture 36, and the free ends of the suture legs 36, shown in FIG. 10, have been cut by the practitioner. The meniscal tear 34 that was torn and loose is now more closely matching normal anatomy and is reinforced with suture 36.

Figure 15:
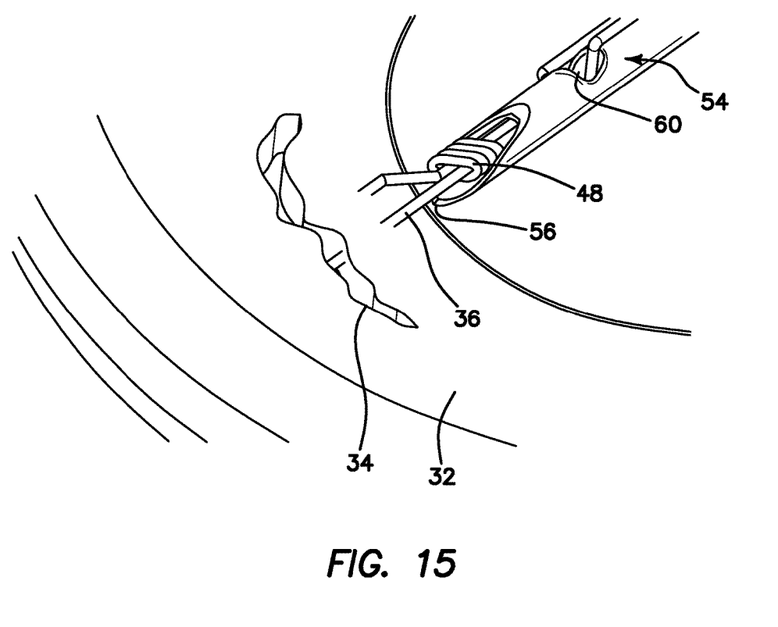
FIG. 15 is a close-up isometric view illustrating the knot pusher of the device cinching down the pre-tied knot onto the meniscus.

FIG. 15 is a close-up isometric view of a knot pusher 54, which is provided for the purpose of cinching down the pre-tied knot 48 on to the meniscus 32. A novel feature of the knot pusher 54 is a dilation tip 56. As illustrated, the dilation tip 56 has a ground triple bevel but any type of sharp point could be utilized to serve the same purpose. The pre-tied knot 48 seats into a knot cavity 58 (FIG. 16) which positions the dilation tip 56 distal to it. That allows the dilation tip 56 to come into contact with the meniscus 32 first. To cinch the pre-tied knot 48 down onto the meniscus 32, the leg of the suture 36 that was captured in the catch needle 18 is retracted, and the knot pusher 54 is advanced. As the dilation tip 56 is advanced toward the meniscus 32, the pointed tip 56 is positioned into the hole that the suture leg is coming out of. Further advancement of the knot pusher 54 allows for dilation of that suture hole with simultaneous advancement of the pre-tied knot 48 into the hole. The knot pusher 54 continues to be advanced, further dilating the suture hole and further advances the pre-tied knot 48 into the meniscus 32 until it is well into the meniscus 32. The knot pusher 54 is then retracted and released from the suture 36 via a knot pusher suture escape slot 60, resulting in the pre-tied knot 48 being cinched well into the meniscus 32 with little or no visibility to it. The benefit of this type of result versus the pre-tied knot 48 being exposed on top of the meniscus 32, or exterior to it, is that there will be little to no abrasion of the knot 48 with the articular cartilage of the femoral condyles. The knot 48 will have a layer of meniscus 32 between it and the articular cartilage.

Figure 16:
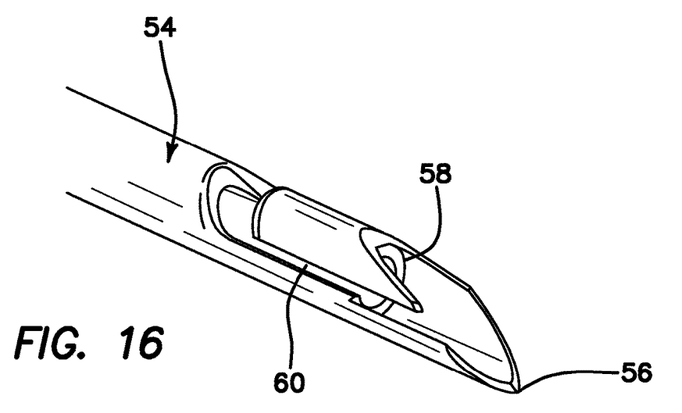
FIG. 16 is an isometric view of the knot pusher of the present invention.

FIG. 16 is an isometric view of the knot pusher 54. The geometry of the knot pusher 54, in particular, is unique relative to other minimally invasive surgical knot pushers because of the dilation tip 56. Once the knot 48 is ready to be cinched, this knot pusher 54 is threaded onto the suture 36 with standard methods, through the suture escape slot 38. The appropriate leg of the suture 36 is retracted, and the knot pusher 54 is advanced, sending the knot 48 toward the meniscus 32. The novel dilation tip 56 which allows for the advancement of the knot 48 into the meniscus 32. It is within the scope of the present invention that the knot pusher 54 may be a telescope sliding type of component that resides on the device shaft proximal to the pre-tied knot 48. During knot advancement, the knot pusher 54 may be detached from the device, allowing for knot pushing. It is also possible that the knot pusher 54 may be a reusable type of device made of appropriate material for autoclaving. It can also be disposable, made of a thermoplastic, and kitted with the device 10 as a separate component.

Figure 17:
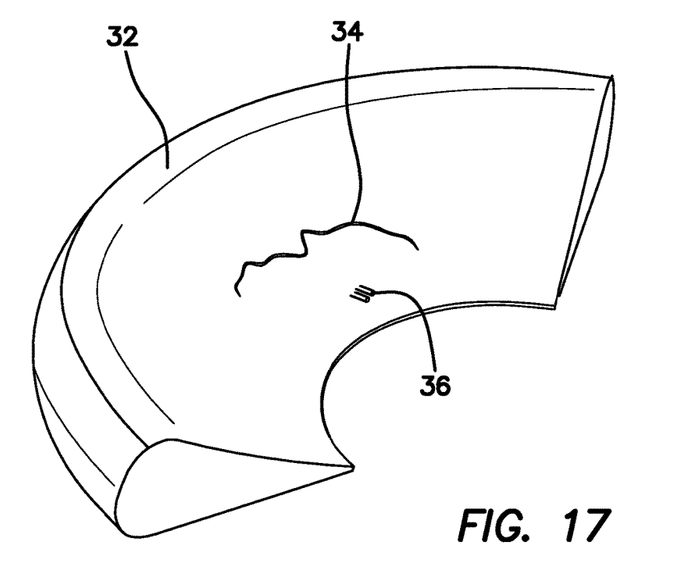
FIG. 17 is an isometric view of the repaired meniscus.

FIG. 17 shows an isometric view of the end result of the inventive meniscal repair procedure, using the above described knot pusher 54. The knot pusher 54 has functioned to dilate the suture hole and has advanced the knot 48 into the meniscus such that it has little to no visibility. The suture ends have been cut and the knot 48 is situated so that it can cause little to no abrasion of articular cartilage. The meniscal tear 34 has been stitched shut, approximating normal anatomy with suture reinforcement.

Of course, while the foregoing invention has been disclosed in connection with the repair of meniscal tissue, it will be recognized that the inventive principles are applicable to many other instances wherein it is desired to repair a tear in a portion of soft tissue.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A method for repairing a tear in a portion of tissue, said method comprising:
    advancing first and second needles into said tissue, so that distal ends of each needle are disposed beyond the tear, wherein the second needle comprises a first window disposed laterally on a first side facing the first needle, the first window having a leading edge, and a second window disposed on a second side opposed to the first side and facing away from the first needle, the second window having a leading edge which is disposed substantially distal to the leading edge of the first window;
    extending a suture needle on which is retained a length of suture from the first needle to the second needle, through said tear, such that the suture needle extends through both the first window and the second window;
    retaining the suture in the second needle by using a spring to move a plunger permanently disposed within the second needle to clamp the suture in place within a lumen of the second needle, thereby ensuring that the suture will be retained within the second needle as the suture needle is retracted therefrom;
    retracting the suture needle back into the first needle; and
    retracting the first and second needles from the tissue, and dispensing suture as the needles are retracted.

2. The method as recited in claim 1, and further comprising a step of sliding a pre-tied knot distally along the suture length toward the location of the tear.

3. The method as recited in claim 2, and further comprising a step of cinching the pre-tied knot.

4. The method as recited in claim 3, and further comprising a step of cutting off the excess suture extending proximally from the pre-tied knot.

5. The method as recited in claim 3, wherein the cinching step comprises a step of advancing a knot pusher distally to push said knot into a hole from which the suture extends.

6. The method as recited in claim 5, wherein the knot pusher t elates the suture hole as it is advanced thereinto.

7. The method as recited in claim 1, wherein during the retaining step, the suture is retained by impact of the plunger against the suture needle and the suture because of the bias imposed by the spring.

8. The method as recited in claim 1, the first needle comprising a window disposed laterally thereon, wherein during the suture needle extending step, the suture needle is advanced through the first needle window.

9. The method as recited in claim 1, wherein the length of suture is retained on a hook of the suture needle.

10. A method for repairing a tear in a portion of tissue, said method comprising:
    advancing first and second needles into said tissue, so that distal ends of each needle are disposed beyond the tear;
    extending a suture needle on which is retained a length of suture from the first needle to the second needle, through said tear;
    retaining the suture in the second needle by using a spring to move a plunger permanently disposed within the second needle to clamp the suture in place within a lumen of the second needle, thereby ensuring that the suture will be retained within the second needle as the suture needle is retracted therefrom;
    retracting the suture needle back into the first needle;
    retracting the first and second needles from the tissue, and dispensing suture as the needles are retracted;
    sliding a pre-tied knot distally along the suture length toward the location of the tear; and
    cinching the pre-tied knot, including advancing a knot pusher distally to push said knot into a hole from which the suture extends, wherein the knot pusher dilates the suture hole as it is advanced thereinto.

* * * * *

UNITED STATES PATENT AND TRADEMARK OFFICE
CERTIFICATE OF CORRECTION

PATENT NO. : 9,724,088 B2
APPLICATION NO. : 14/466661
DATED : August 8, 2017
INVENTOR(S) : Nicanor A. Domingo Page 1 of 1

It is certified that error appears in the above-identified patent and that said Letters Patent is hereby corrected as shown below:

On the Title Page

On page 2, in Column 2, item (56) under "Other Publications", Line 45-46, delete "international" and insert --International-- therefor In the Claims In Column 10, Line 8, in Claim 6, delete "t elates" and insert --dilates-- therefor Signed and Sealed this
Twelfth Day of June, 2018

Andrei Iancu
*Director of the United States Patent and Trademark Office*